US006350759B1

(12) United States Patent
Casara et al.

(10) Patent No.: US 6,350,759 B1
(45) Date of Patent: Feb. 26, 2002

(54) DIHYDRO- AND TETRAHYDRO-QUINOLINE COMPOUNDS

(75) Inventors: Patrick Casara, Villennes sur Seine; Gilbert Dorey, Versailles; Pierre Lestage, La Celle Saint Cloud; Brian Lockhart, Croissy sur Seine, all of (FR)

(73) Assignee: Adir et Compagnie, Courbevoie (FR)

( * ) Notice: Subject to any disclaimer, the term of this patent is extended or adjusted under 35 U.S.C. 154(b) by 0 days.

(21) Appl. No.: 09/425,267

(22) Filed: Oct. 22, 1999

(30) Foreign Application Priority Data

Oct. 23, 1998 (FR) .............................. 98 13306

(51) Int. Cl.$^7$ .............................. A61K 31/47
(52) U.S. Cl. .................. 514/311; 514/312; 514/313; 514/314; 544/179
(58) Field of Search ................ 514/311, 312, 514/314, 313; 544/179

(56) References Cited

U.S. PATENT DOCUMENTS 3,331,846 A * 7/1967 Easton et al. ............... 260/280
5,688,810 A * 11/1997 Jones et al. ................. 514/311

OTHER PUBLICATIONS

CAPLUS DN 128:34752, Jones et al., US 5688810 A (1997), abstract only.*
CAPLUS DN 128:48145, Suzuki et al., JP 09301953 A2, (1997), abstract only.*
CAPLUS DN 123:338842, Weber et al., Pharmazie (1995), 50(5), 365–366, abstract only.*
CAPLUS DN 114:142756, Barmettler et al., Helv. Chim. Acta. (1990), 73(6), 1515–1573, abstract only.*
CAPLUS DN 113:40418, De et al., Indian J. Chem., Sect. B (1990), 29B(1), 70–1, abstract only.*
CAPLUS DN 104:5752 Tsushima et al., Agric. Biol. Chem. (1985), 49 (8), 2421–2423, abstract only.*

* cited by examiner

Primary Examiner—Marianne C. Seidel
Assistant Examiner—C. Delacroix-Muirheld

(74) Attorney, Agent, or Firm—The Firm of Hueschen and Sage; G. Patrick Sage

(57) ABSTRACT

Compound of formula (I):

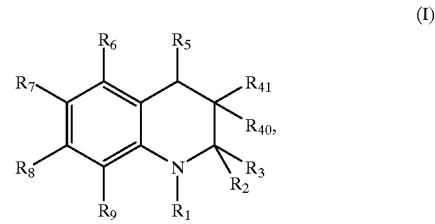

(I)

wherein:

$R_1$ represents hydrogen or

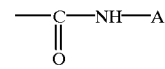

wherein A is as defined in the description, $R_2$ and $R_3$ each independently represents alkyl, cycloalkyl, heterocycloalkyl, optionally substituted aryl, optionally substituted heteroaryl, cycloalkylalkyl, heterocycloalkylalkyl, optionally substituted arylalkyl, optionally substituted heteroarylalkyl, or optionally substituted aminoalkyl or $R_2$ and $R_3$, together with the carbon atom carrying them, form cycloalkyl or monocyclic heterocyclic group, substituted or unsubstituted, $R_{40}$ represents hydrogen or a group selected from optionally substituted alkyl, optionally substituted alkenyl and optionally substituted alkynyl or Q or —V—Q wherein V represents alkylene, alkenylene or alkynylene and Q represents optionally substituted cycloalkyl, optionally substituted aryl, optionally substituted heterocycloalkyl, or optionally substituted heteroaryl, $R_{41}$ and $R_5$ together form a bond or each represents hydrogen, $R_6$, $R_7$, $R_8$ and $R_9$ each independently represents hydrogen, halogen, alkyl, ($C_3$–$C_8$)cycloalkyl, or —OW wherein W is as defined in the description, and medicinal products containing the same which are useful as antioxidative agents.

14 Claims, No Drawings

DIHYDRO- AND TETRAHYDRO-QUINOLINE COMPOUNDS

DESCRIPTION OF THE PRIOR ART

The preparation of compounds having a 1,2-dihydroquinoline structure has been described in Patent Specifications DD 227 434 and DE 4 115 535. Other compounds having the same nucleus, variously substituted, have been used in the preparation of smoked meats (GB 1537334) or as photochemical indicators (WO 89 05994). The anti-oxidant properties of tetrahydroquinoline compounds have been used in the field of lubricants (EP 072 349). Compounds of this type have also been described as inhibitors of lipid absorption (EP 028 765).

BACKGROUND OF THE INVENTION

According to Hartman's free-radical theory of ageing (J. Gerontol., 1956, 11, 298), successive oxidation attacks create "oxidation stress" conditions, which reflect an imbalance in the organism between the systems that produce free-radical species and the systems that are protective against those species (R. E. PACIFICI, K. J. A. DAVIES, Gerontology, 1991, 37, 166). Various defence mechanisms may act in synergy, allowing the action of the free radicals to be controlled. Those mechanisms may be enzymatic, as is the case for systems involving superoxide dismutase, catalase and glutathione peroxidase, or non-enzymatic in the case of vitamin E and vitamin C involvement. With age, however, those natural defences become less and less efficient, especially as a result of the oxidative inactivation of a large number of enzymes (A. CASTRES de PAULET, Ann. Biol. Clin., 1990, 48, 323).

It has been possible to link conditions of oxidation stress with disorders associated with ageing, namely atherosclerosis, cataract, non-insulin-dependent diabetes and cancer (M. HAYN et al., Life Science, 1996, 59, 537). The central nervous system is especially sensitive to oxidation stress because of its high oxygen consumption, the relatively low level of its anti-oxidation defences and the high iron content of some cerebral regions (S. A. BENKOVIC et al., J. Comp. Neurol. 1993, 338, 92; D. HARTMAN, Drugs Aging, 1993, 3, 60). Successive oxidation attacks therefore constitute one of the main etiological factors of cerebral ageing and associated disorders, namely Alzheimer's disease and chronic neurodegenerative disorders, neurodegeneracies of the basal ganglia (Parkinson's disease, Huntington's disease,.), (B. HALLIWELL, J. Neurochem., 1992, 59, 1609).

In addition to the fact that the compounds of the present invention are new, they exhibit valuable pharmacological properties. Their anti-oxidant character, being a trap for reactive oxygenated species, especially at the level of the central nervous system, means that they can be considered for use in opposing the effects of oxidation stress, especially at the cerebral level. Most of them, moreover, have the advantage of not causing a hypothermic effect at the doses used for obtaining neuroprotective action. They will therefore be useful in the treatment of disorders associated with ageing, such as atherosclerosis and cataract, in the treatment of cancer, in the treatment of cognitive disorders, and in the treatment of acute neurodegenerative disorders, such as cerebral ischaemia and epilepsy, and in the treatment of chronic neurodegenerative disorders, such as Alzheimer's disease, Pick's disease and neurodegeneracies of the basal ganglia (Parkinson's disease, Huntington's disease).

DETAILED DESCRIPTION OF THE INVENTION

The present invention relates especially to the compounds of the general formula (I):

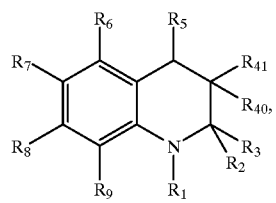

wherein:
$R_1$ represents a hydrogen atom or a group

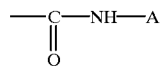

wherein A represents a hydrogen atom or a group —$BNZ_1Z_2$ in which B represents a linear or branched ($C_1$–$C_6$)alkylene group and $Z_1$ and $Z_2$ independently represent a hydrogen atom or an alkyl, ($C_3$–$C_8$) cycloalkyl or optionally substituted aryl group or, together with the nitrogen atom carrying them, form an optionally substituted heterocycloalkyl or heteroaryl group, $R_2$ and $R_3$ each independently represents an alkyl group, a ($C_3$–$C_8$)cycloalkyl group, a heterocycloalkyl group, an optionally substituted aryl group, an optionally substituted heteroaryl group, a cycloalkylalkyl group, a heterocycloalkylalkyl group, an optionally substituted arylalkyl group, an optionally substituted heteroarylalkyl group or an aminoalkyl group (optionally substituted on the nitrogen atom by one or two groups selected from alkyl, cycloalkyl, aryl and arylalkyl) or $R_2$ and $R_3$, together with the carbon atom carrying them, form a ($C_3$–$C_8$)cycloalkyl group or a monocyclic heterocycloalkyl group unsubstituted or substituted by an alkyl, cycloalkyl, cycloalkylalkyl, aryl or arylalkyl group, $R_{40}$ represents a hydrogen atom or a group selected from optionally substituted alkyl, optionally substituted alkenyl and optionally substituted alkynyl or a group Q or —V—Q wherein V represents an alkylene, alkenylene or alkynylene group and Q represents an optionally substituted ($C_3$–$C_8$)cycloalkyl group, an optionally substituted aryl group, an optionally substituted heterocycloalkyl group or an optionally substituted heteroaryl group, $R_{41}$ and $R_5$ together form a bond or each represents a hydrogen atom, $R_6$, $R_7$, $R_8$ and $R_9$ each independently represents a hydrogen atom, a halogen atom, an alkyl group, a ($C_3$–$C_8$) cycloalkyl group or a group —OW wherein W represents a hydrogen atom or an alkyl group, an acyl group, a ($C_3$–$C_8$)cycloalkyl group, a heterocycloalkyl group, an optionally substituted aryl group, an optionally substituted heteroaryl group, an optionally substituted arylalkyl group or an optionally substituted heteroarylalkyl group (provided that $R_6$, $R_7$, $R_8$ and $R_9$ cannot all simultaneously represent a hydrogen atom and that at least one of them represents a group —OW as defined hereinbefore), with the proviso that:
when $R_2$ and $R_3$ represent an alkyl group:
if each of $R_6$ to $R_9$ independently represents a hydrogen atom, an alkyl group or a group —OW wherein W represents an alkyl group, and $R_{41}$ and $R_5$ together form a bond, then $R_{40}$ is other than a hydrogen atom or an alkyl group, if a single group —OW is present in the molecule and represents a hydroxy group, then $R_{40}$ is other than a hydrogen atom, if a single group —OW is present in the molecule and represents a methoxy group, then $R_{40}$ is other than a hydroxyalkyl group, the compound of formula (I) being other than 7-methoxy-2,2-diphenyl-1,2-dihydroquinoline, it being understood that:

the term alkyl denotes a linear or branched chain of from 1 to 6 carbon atoms, the term acyl denotes an alkyl-carbonyl group, alkyl being as defined hereinbefore, the term alkenyl denotes a linear or branched chain of from 2 to 6 carbon atoms containing from 1 to 3 double bond(s), the term alkynyl denotes a linear or branched chain of from 2 to 6 carbon atoms containing from 1 to 3 triple bond(s), the term alkylene denotes a linear or branched bivalent group containing from 1 to 6 carbon atoms, the term alkenylene denotes a linear or branched bivalent group containing from 2 to 6 carbon atoms and from 1 to 3 double bonds, the term alkynylene denotes a linear or branched bivalent group containing from 2 to 6 carbon atoms and from 1 to 3 triple bonds, the term aryl denotes a phenyl, naphthyl or biphenyl group, the term heterocycloalkyl denotes a mono- or bi-cyclic, 4- to 11-membered group containing from 1 to 6 hetero atoms selected from nitrogen, oxygen and sulphur, it being possible for the group to contain one or more unsaturations without thereby having an aromatic character, the term heteroaryl denotes an aromatic or partially aromatic, mono- or bi-cyclic, 4- to 11-membered group containing from 1 to 6 hetero atoms selected from nitrogen, oxygen and sulphur, the term substituted used in respect of the expressions aryl and arylalkyl indicates that the groups concerned are substituted by one or more halogen atoms or alkyl, linear or branched $(C_1-C_6)$alkoxy, linear or branched $(C_1-C_6)$perhaloalkyl, amino (optionally substituted by 1 or 2 alkyl groups), cyano, carboxy, linear or branched $(C_1-C_6)$alkoxycarbonyl, aminocarbonyl (optionally substituted on the nitrogen atom by 1 or 2 alkyl groups), nitro or hydroxy groups, the term substituted used in respect of the expressions alkyl, alkenyl, alkynyl and cycloalkyl indicates that such groups are substituted by one or more groups selected from hydroxy, linear or branched $(C_1-C_6)$alkoxy, linear or branched $(C_1-C_6)$alkylthio, amino (optionally substituted by one or two alkyl groups), carboxy, nitro, cyano, linear or branched $(C_1-C_6)$alkoxycarbonyl and aminocarbonyl (optionally substituted on the nitrogen atom by one or two alkyl groups), the term substituted used in respect of the expressions heterocycloalkyl, heteroaryl and heteroarylalkyl indicates that the groups concerned are substituted by one or more halogen atoms or alkyl, linear or branched $(C_1-C_6)$alkoxy, linear or branched $(C_1-C_6)$perhaloalkyl, amino (optionally substituted by 1 or 2 alkyl groups), cyano, carboxy, linear or branched $(C_1-C_6)$alkoxycarbonyl, aminocarbonyl (optionally substituted on the nitrogen atom by 1 or 2 alkyl groups), nitro, hydroxy or oxo groups, enantiomers and diastereoisomers thereof, and addition salts thereof with a pharmaceutically acceptable acid or base.

Amongst the pharmaceutically acceptable acids there may be mentioned, without implying any limitation, hydrochloric, hydrobromic, sulphuric, phosphonic, acetic, trifluoroacetic, lactic, pyruvic, malonic, succinic, glutaric, fumaric, tartaric, maleic, citric, ascorbic, methanesulphonic, camphoric and oxalic acid etc.

Amongst the pharmaceutically acceptable bases there may be mentioned, without implying any limitation, sodium hydroxide, potassium hydroxide, triethylamine, tert-butylamine etc.

The present invention advantageously relates to compounds of formula (I) wherein $R_1$ represents a hydrogen atom.

Preferably, in the compounds of formula (I), $R_6$, $R_7$, $R_8$ and $R_9$ each independently represents a hydrogen atom, an alkyl group or a group —OW wherein W represents an alkyl, acyl or phenyl group. More especially, W represents an alkyl group.

Preferred compounds of the invention are those wherein $R_2$ and $R_3$ each represents an alkyl group, for example methyl.

Other preferred compounds of the invention are those wherein $R_2$ and $R_3$ together form an optionally substituted cycloalkyl or heterocycloalkyl group, and more especially, a cycloalkyl group, for example cyclohexyl.

In the compounds of formula (I), $R_{40}$ preferably represents a hydrogen atom or a group V—Q, V being more especially an alkylene group and Q being more especially a heterocycloalkyl group.

The preferred aryl group of the invention is the phenyl group.

An advantageous aspect of the invention relates to compounds of formula (I) wherein $R_1$ represents a hydrogen atom, $R_2$ and $R_3$ represent an alkyl group or together form a cycloalkyl group, $R_{40}$ represents a hydrogen atom or a group —V—Q wherein V represents an alkylene group and Q represents a heterocycloalkyl group, and $R_6$, $R_7$, $R_8$ and $R_9$ each independently represents a hydrogen atom, an alkyl group or a group —OW wherein W represents an alkyl, acyl or phenyl group, it being understood that $R_6$, $R_7$, $R_8$ and $R_9$ cannot all represent a hydrogen atom and that at least one of them represents a group —OW as defined hereinbefore.

Amongst the preferred compounds of the invention there may be mentioned:

6-ethoxy-1,2-dihydroquinoline-2-spirocyclohexane, 6-ethoxy-5,7,8-trimethyl-1,2-dihydroquinoline-2-spirocyclohexane, 8-ethoxy-1,2-dihydroquinoline-2-spirocyclohexane, 5,7-diisopropyl-6-ethoxy-1,2-dihydroquinoline-2-spirocyclohexane, 5,7-dimethyl-6-ethoxy-1,2-dihydroquinoline-2-spirocyclohexane, 6-ethoxy-2,2,5,7,8-pentamethyl-1,2,3,4-tetrahydroquinoline, 5,7-diisopropyl-2,2-dimethyl-6-ethoxy-1,2,3,4-tetrahydroquinoline, 6-ethoxy-2,2,5,7-tetramethyl-1,2,3,4-tetrahydroquinoline, 6-ethoxy-5,7,8-trimethyl-1,2,3,4-tetrahydroquinoline-2-spirocyclohexane, 6-ethoxy-1,2-dihydroquinoline-2-spiro-4'-piperidine, 6-ethoxy-1,2-dihydroquinoline-2-spiro-4'-(1'-cyclopropylmethyl-piperidine), 2,2-dimethyl-6-ethoxy-3-(2-morpholinoethyl)-1,2-dihydroquinoline dihydrochloride, 6-tert-butoxy-1,2-dihydroquinoline-2-spirocyclohexane, 6-methoxy-1,2-dihydroquinoline-2-spirocyclohexane, 6-phenoxy-1,2-dihydroquinoline-2-spirocyclohexane, 6-ethoxy-5,7-dimethyl-1,2,3,4-tetrahydroquinoline-2-spirocyclohexane, 6-ethoxy-2,2-dimethyl-3-[2-(2,6-dioxopiperazin-4-yl)ethyl]-1,2-dihydroquinoline, 6-ethoxy-2,2-dimethyl-3-[2-(1-piperidinyl)ethyl]-1,2-dihydroquinoline.

2-[2-(6-ethoxy-2,2-dimethyl-1 2-dihydro-3-yl)ethyl]-1H-isoindole-1,3(2H)-dione,

3-[2-(6-ethoxy-2,2-dimethyl-1,2-dihydro-3-quinolenyl)ethyl]-4(3H)-quinazolinone, 6-tert-butylcarbonyloxy-1,2-dihydroquinoline-2-spirocyclohexane, and very especially:

6-ethoxy-2,2,5,7,8-pentamethyl-1,2,3,4-tetrahydroquinoline, 6-ethoxy-1,2-dihydroquinoline-2-spirocyclohexane.

The present invention relates also to a process for the preparation of the compounds of formula (I), which is characterised in that there is used as starting material a variously substituted aniline of formula (II):

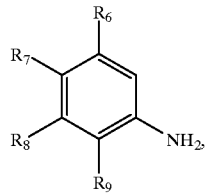

(II)

wherein $R_6$, $R_7$, $R_8$ and $R_9$ are as defined for formula (I), which is subjected:

either to the action, in a basic medium and optionally in the presence of a catalyst, of a halogenated acetylide of formula (III):

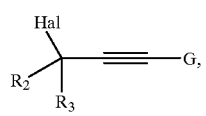

(III)

wherein $R_2$ and $R_3$ are as defined for formula (I), G represents a hydrogen atom or a trialkylsilyl group and Hal represents a halogen atom, to yield a compound of formula (IV):

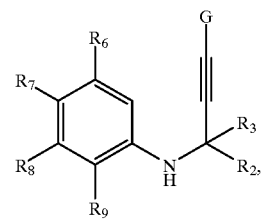

(IV)

wherein $R_2$, $R_3$, $R_6$, $R_7$, $R_8$, $R_9$ and G are as defined hereinbefore, or to the action of a carbonyl compound of formula (V):

(V)

wherein $R_2$ and $R_3$ are as defined for formula (I), to yield a compound of formula (VI):

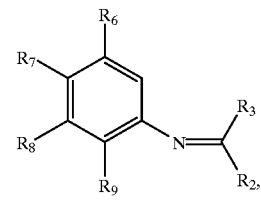

(VI)

wherein $R_2$, $R_3$, $R_6$, $R_7$, $R_8$ and $R_9$ are as defined hereinbefore, which compound (VI) is subjected, in a basic medium, to the action of an acetylide of formula (III) as defined hereinbefore, to yield a compound of formula (IV) as defined hereinbefore, which compound of formula (IV), where applicable after cleavage of the trialkylsilyl group, is cyclised by heating in the presence of an appropriate catalyst to yield a compound of formula (I/a):

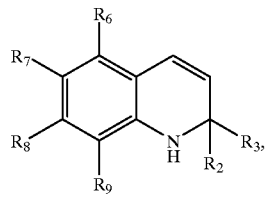

(I/a)

a particular case of the compounds of formula (I) wherein $R_2$, $R_3$, $R_6$, $R_7$, $R_8$ and $R_9$ are as defined hereinbefore, which:

⇥ either may be subjected to a reduction reaction to yield a compound of formula (I/b):

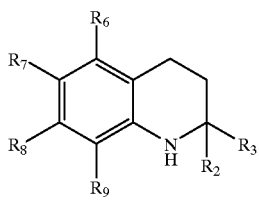

(I/b)

a particular case of the compounds of formula (I) wherein $R_2$, $R_3$, $R_6$, $R_7$, $R_8$ and $R_9$ are as defined hereinbefore, which compounds of formula (I/a) and (I/b), after chloroformylation of the ring nitrogen, are subjected to the action of an amine of formula (VII):

$$H_2N-A \qquad (VII),$$

wherein A is as defined for formula (I), to yield a compound of formula (I/c):

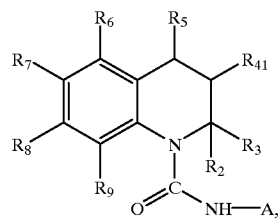

(I/c)

wherein $R_2$, $R_3$, $R_6$, $R_7$, $R_8$, $R_9$ and A are as defined hereinbefore, and $R_{41}$ and $R_5$ are as defined for formula (I), ♮ or, after protection of the ring nitrogen atom, may be subjected successively to a hydroxyhalogenation reaction and to an oxidation reaction in the benzyl position to yield a compound of formula (VIII):

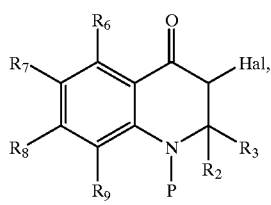

(VIII)

wherein $R_2$, $R_3$, $R_6$, $R_7$, $R_8$ and $R_9$ are as defined hereinbefore, Hal represents a halogen atom and P is a protecting group for the ring nitrogen (for example an acetyl, trifluoroacetyl, tert-butoxycarbonyl or benzyloxycarbonyl group), which is subjected to a nucleophilic substitution reaction to yield a compound of formula (IX):

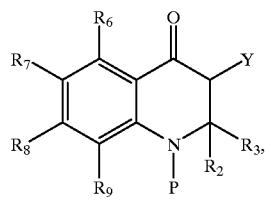

(IX)

wherein $R_2$, $R_3$, $R_6$, $R_7$, $R_8$, $R_9$ and P are as defined hereinbefore and Y represents either a group $R_{40}$, which is as defined for formula (I) but is other than a hydrogen atom, or a precursor of such a group, which, after deprotection of the ring nitrogen, is subjected to a reduction reaction of the carbonyl function, followed by an elimination reaction to yield a compound of formula (X):

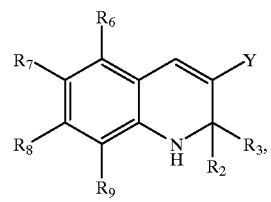

(X)

wherein $R_2$, $R_3$, $R_6$, $R_7$, $R_8$, $R_9$ and Y are as defined hereinbefore, which compound of formula (X) may, when Y is a precursor of a group $R_{40}$ as defined hereinbefore, be subjected to a succession of conventional reactions directed at yielding a compound of formula (I/d):

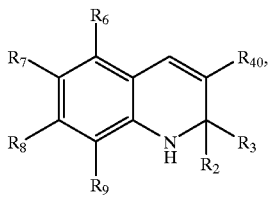

(I/d)

a particular case of the compounds of formula (I) wherein $R_2$, $R_3$, $R_6$, $R_7$, $R_8$, $R_9$ and $R_{40}$ are as defined hereinbefore, which may be reduced to yield a compound of formula (I/e):

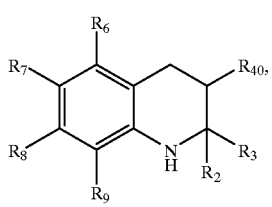

(I/e)

a particular case of the compounds of formula (I) wherein $R_2$, $R_3$, $R_{40}$, $R_6$, $R_7$, $R_8$ and $R_9$ are as defined hereinbefore, which compounds (I/d) and (I/e), after chloroformylation of the ring nitrogen, are subjected to the action of an amine of formula (VII) as defined hereinbefore to yield a compound of formula (I/f):

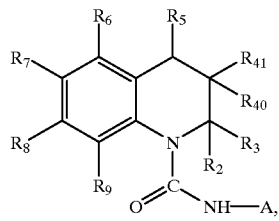

(I/f)

wherein $R_2$, $R_3$, $R_6$, $R_7$, $R_8$, $R_9$ and A are as defined hereinbefore, $R_{40}$ has the same meanings as in formula (I) other than a hydrogen atom, and $R_4$ and $R_5$ are as defined for formula (I), the compounds (I/a) to (I/f) constituting the totality of the compounds of formula (I):

which may be, if necessary, purified according to a conventional purification technique, the stereoisomers of which are, where appropriate, separated according to a conventional separation technique, which are, if desired, converted into their addition salts with a pharmaceutically acceptable acid or base.

The present invention relates also to pharmaceutical compositions comprising as active ingredient at least one compound of formula (I) alone or in combination with one or more inert, non-toxic excipients or carriers.

Amongst the pharmaceutical compositions according to the invention there may be mentioned more especially those that are suitable for oral, parenteral and nasal administration, tablets or dragées, sublingual tablets, gelatin capsules, lozenges, suppositories, creams, ointments, dermal gels etc.

The dosage used varies according to the sex, age and weight of the patient, the nature and the severity of the disorder and the administration route, which may be oral, nasal or parenteral. Generally, the unit dose ranges from 0.1 to 500 mg for a treatment in from 1 to 3 administrations per 24 hours.

The following Examples illustrate the invention but do not limit it in any way.

The starting materials used are known products or are prepared according to known procedures.

Preparation A

4-Ethoxy-3,5,6-trimethylaniline

Step 1:

2-Ethoxy-1,3,4-trimethylbenzene 734 mmol (101.5 g) of potassium carbonate and 917 mmol (143.1 g) of ethyl iodide are added in succession to a solution of 367 mmol (50 g) of 2,3,6-trimethylphenol in 1500 ml of acetonitrile. The whole is heated at reflux for 48 hours. The reaction mixture is subsequently cooled and then filtered and the filtrate is concentrated. The residue obtained is dissolved in ethyl acetate and washed with water and then with 10% aqueous sodium chloride solution. After drying the organic phase and then concentrating, an oily residue is obtained which is purified by chromatography on silica gel, using a petroleum ether: ethyl acetate mixture 95:5 as eluant, to yield the expected product.

Step 2:

4-Ethoxy-3,5,6-trimethyl-iodobenzene 222 mmol (50 g) of N-iodosuccinimide are added to a solution of 171 mmol (28.03 g) of the compound described in the above Step in 650 ml of acetonitrile and the whole is heated at reflux for 24 hours. The solvent is then evaporated off in vacuo and the residue is taken up in ether. The solution is washed with saturated $NaHCO_3$ solution and then with 10% aqueous sodium chloride solution. The organic phase is dried and concentrated. The oily residue obtained is purified by chromatography on silica gel, using a petroleum ether ethyl acetate mixture 95:5 as eluant, to yield the expected product.

Step 3:

4-Ethoxy-3,5,6-trimethylaniline 0.46 mmol (0.426 g) of $Pd_2(dba)_3$ and 1.39 mmol (0.947 g) of BINAP are introduced into a 1-litre round-bottomed flask under an inert atmosphere. In a second round-bottomed flask. 46.5 mmol (13.5 g) of the compound described in the above Step, 65.1 mmol (6.26 g) of sodium tert-butanolate, 65.1 mmol (17.21 g) of 18 crown 6 and 65.8 mmol (10.12 g) of benzophenone imine are dissolved in 250 ml of anhydrous THF. The solution in the second round-bottomed flask is introduced into the round-bottomed flask containing the catalytic system with the aid of a cannula. The whole is heated at 60° C. for 3 hours and then the reaction mixture is diluted with ether. The precipitate formed is filtered over fritted glass and the filtrate is then evaporated. The residue obtained is redissolved in 300 ml of THF. 30 ml of hydrochloric acid solution (2N) are added thereto and the solution is stirred at ambient temperature for 1 hour. The whole is then diluted with excess hydrochloric acid (1N) and a heptane:ethyl acetate mixture 2:1. The aqueous phase is separated and then neutralised using 1M sodium hydroxide solution. After extracting with dichloromethane, drying the organic phase and evaporating off the solvent, the expected product is obtained.

Preparation B 3,5-Diisopropyl-4-ethoxyaniline

Step 1:

2,6-Diisopropyl-4-nitrophenol 78.3 mmol (4.93 g) of fuming nitric acid are added dropwise to a solution, cooled to 0° C., of 53.9 mmol (9.62 g) of 2,6-diisopropylphenol in 350 ml of acetic acid. The reaction mixture is stirred at 0° C. for 1 hour 30 minutes and is then poured into a mixture of ethyl acetate and ice. The organic phase is isolated and then washed with water. After drying and evaporating off the solvent, an oily residue is recovered which is purified by chromatography on silica gel using a petroleum ether: ethyl acetate mixture 9:1 as eluant.

Step 2:

2,6-Diisopropyl-1-ethoxy-4-nitrobenzene

The expected product is obtained according to the procedure described in Step 1 of Preparation A, starting from the compound described in the above Step.

Step 3:

3,5-Diisopropyl-4-ethoxyaniline

A solution of 19.9 mmol (5.0 g) of the compound described in the above Step in 135 ml of absolute ethanol in the presence of 1.5 g of palladium-on-carbon (10%) is placed under 1 atm. of hydrogen at ambient temperature for 4 hours. After that period, the reaction mixture is filtered and then the filtrate is concentrated to yield the expected compound.

Preparation C

3,5-Dimethyl-4-ethoxyaniline

Step 1:

3,5-Dimethyl-4-ethoxy-nitrobenzene 300 mmol (326 g) of caesium carbonate and 374 mmol (58.5 g) of ethyl iodide are added in succession to a solution of 149.5 mmol (25 g) of 2,6-dimethyl-4-nitrophenol in 1300 ml of acetonitrile. The whole is heated at reflux under an inert atmosphere for 15 hours. The reaction mixture is subsequently cooled and then filtered, and the filtrate is evaporated. The residue is dissolved in ethyl acetate and washed with water and then with 10% aqueous sodium chloride solution. The expected product is obtained by drying the organic phase and then concentrating.

Step 2:

3,5-Dimethyl-4-ethoxyaniline

A solution of 149.5 mmol (29.19 g) of the compound described in the above Step in 1000 ml of absolute ethanol in the presence of 9.4 g of palladium-on-carbon (10%) is placed under 1 atm. of hydrogen at ambient temperature for 4 hours. After that period, the reaction mixture is filtered and then the filtrate is concentrated to yield the expected compound.

Preparation D

4-tert-Butoxy-aniline

Step 1:

1-tert-Butoxy-4-nitrobenzene 43.79 mmol of N-N-dimethylformamide di-tert-butyl acetal are added, at ambient temperature, to a solution of 10.78 mmol (1.5 g) of 4-nitrophenol in 10 ml of toluene. The reaction mixture is heated at reflux, with vigorous stirring, for 5 hours. The reaction mixture is diluted with ethyl acetate and then washed with water, with saturated aqueous sodium bicarbonate solution and then with 10% aqueous sodium chloride solution. The expected product is obtained by drying the organic phase and then concentrating.

Step 2:

4-tert-Butoxy-aniline

A solution of 4.61 mmol (0.90 g) of the compound described in the above Step in 15 ml of absolute ethanol containing 24.65 mmol (2.12 g) of cyclohexene and 0.29 g of palladium-on-carbon (10%) is heated at reflux, with vigorous stirring, for 2 hours. After that period, the reaction mixture is filtered and then the filtrate is concentrated to yield the expected compound.

Preparation E

4-tert-Butylcarbonyloxy-aniline

Step 1:

1-tert-Butylcarbonyloxy-4-nitrobenzene 161.1 mmol (19.48 g) of pivaloyl chloride are added, at 0° C., to a solution of 107.8 mmol (15 g) of 4-nitrophenol in 250 ml of pyridine. The reaction mixture is stirred for 72 hours at ambient temperature. The reaction mixture is evaporated in vacuo and the oily residue is diluted with ethyl acetate and then washed with aqueous hydrochloric acid solution (0.1N) and then with 10% aqueous sodium chloride solution. The expected product is obtained by drying the organic phase and then concentrating.

Step 2:

4-tert-Butylcarbonyloxy-aniline

A solution of 95.41 mmol (21.30 g) of the compound described in the above Step in 1200 ml of a 4/1 mixture of methanol and acetic acid containing 573 mmol (32.00 g) of iron is heated at 65° C. for 20 hours. After that period, the reaction mixture is filtered and the filtrate is then concentrated to yield an oily residue which is diluted with ethyl acetate and washed with 10% aqueous sodium bicarbonate solution and then with 10% aqueous sodium chloride solution. The expected product is obtained by drying the organic phase and then concentrating.

EXAMPLE 1

6-Ethoxy-1,2-dihydroquinoline-2-spirocyclohexane hydrochloride

Step 1:

N-(4-Ethoxyphenyl)-N-[1-(1-ethynyl)cyclohexyl]amine

To a solution, cooled to 10° C., of 18.2 mmol (2.5 g) of p-phenetidine in a mixture of ether:water (4:1; 30 ml) containing 24.5 mmol (3.42 ml) of triethylamine there are added, in succession, 0.25 mmol (0.025 g) of CuCl, 0.39 mmol (0.025 g) of Cu and, dropwise, 28.0 mmol (4.0 g) of 1-ethynyl-1-chlorocyclohexane prepared according to the method described in J. Am. Chem. Soc., 83, 725, 1961, starting from 1-ethynylcyclohexanol. After stirring for 4 hours (allowing the temperature to increase towards ambient temperature) the reaction mixture is diluted with ether and then washed with 1N sulphuric acid solution. The ethereal phase is removed and the aqueous phase is neutralised (at 0° C.) using potassium hydroxide pellets and then re-extracted with ether. The organic phase is dried and then concentrated to yield the expected product.

Step 2:

6-Ethoxy-1,2-dihydroquinoline-2-spirocyclohexane hydrochloride 3.0 mmol (0.30 g) of CuCl are added to a solution of 14.79 mmol (2.89 g) of the compound described in the above Step in 20 ml of toluene and the whole is heated at reflux for 40 minutes. The solvent is then evaporated off and the oily residue is purified by chromatography on silica gel, using dichloromethane as eluant, to yield the expected product.

The latter is precipitated in hydrochloride form from an ethereal hydrogen chloride/isopropanol mixture to yield the corresponding hydrochloride.

Melting point: 183°–186° C. (decomposition, $iPr_2O$/$CH_2Cl_2$); Elemental microanalysis (empirical formula: $C_{16}H_{21}NO.HCl$).

|              | C     | H    | N    | Cl    |
|--------------|-------|------|------|-------|
| % found      | 68.50 | 7.87 | 5.08 | 12.67 |
| % calculated | 68.68 | 7.92 | 5.01 | 12.61 |

EXAMPLE 2

6-Ethoxy-5,7,8-trimethyl-1,2-dihydroquinoline-2-spirocyclohexane hydrochloride Step 1:

N-(4-Ethoxy-2,3,5-trimethylphenyl)-N-[1-(1-ethynyl)cyclohexyl]amine

The expected product is obtained according to the procedure described in Step 1 of Example 1, starting from the compound described in Preparation A.

Step 2:

6-Ethoxy-5,7,8-trimethyl-1,2-dihydroquinoline-2-spirocyclohexane hydrochloride

The expected product is obtained according to the procedure described in Step 2 of Example 1, starting from the compound described in the above Step.

The corresponding hydrochloride is obtained by precipitation from an ether/dichloromethane mixture to which ethereal hydrogen chloride is added.

Melting point: 158°–161° C. (Et$_2$O/CH$_2$Cl$_2$); Elemental microanalysis (empirical formula: C$_{19}$H$_{27}$NO.HCl).

|  | C | H | N | Cl |
|---|---|---|---|---|
| % found | 71.13 | 8.68 | 4.30 | 11.24 |
| % calculated | 70.90 | 8.77 | 4.35 | 11.01 |

EXAMPLE 3

8-Ethoxy-1,2-dihydroquinoline-2-spirocyclohexane hydrochloride

Step 1:

N-(2-Ethoxyphenyl)-N-[1-(1-ethynyl)cyclohexyl]amine

The expected product is obtained according to the procedure described in Step 1 of Example 1, with replacement of the p-phenetidine by o-phenetidine.

Step 2:

8-Ethoxy-1,2-dihydroquinoline-2-spirocyclohexane hydrochloride

The expected product is obtained according to the procedure described in Step 2 of Example 1, starting from the compound described in the above Step. The corresponding hydrochloride is obtained by precipitation from an ether/dichloromethane mixture to which ethereal hydrogen chloride is added.

Melting point: 154°–155° C. (Et$_2$O/CH$_2$Cl$_2$); Elemental microanalysis (empirical formula: C$_{16}$H$_{21}$NO.HCl).

|  | C | H | N | Cl |
|---|---|---|---|---|
| % found | 68.62 | 7.65 | 4.84 | 12.59 |
| % calculated | 68.68 | 7.92 | 5.01 | 12.67 |

EXAMPLE 4

5,7-Diisopropyl-6-ethoxy-1,2-dihydroquinoline-2-spirocyclohexane hydrochloride Step 1:

N-(3,5-Diisopropyl-4-ethoxyphenyl)-N-[1-(1-ethynyl)cyclohexyl]amine

The expected product is obtained according to the procedure described in Step 1 of Example 1, using as starting material the compound described in Preparation B.

Step 2:

5,7-Diisopropyl-6-ethoxy-1,2-dihydroquinoline-2-spirocyclohexane hydrochloride

The expected product is obtained according to the procedure described in Step 2 of Example 1, starting from the compound described in the above Step.

Melting point: 166°–169° C. (with decomposition; Et$_2$O); Elemental microanalysis (empirical formula: C$_{22}$H$_{33}$NO.HCl).

|  | C | H | N | Cl |
|---|---|---|---|---|
| % found | 72.87 | 9.28 | 3.87 | 9.76 |
| % calculated | 72.60 | 9.42 | 3.85 | 9.74 |

EXAMPLE 5

5,7-Dimethyl-6-ethoxy-1,2-dihydroquinoline-2-spirocyclohexane hydrochloride

Step 1:

N-(3,5-Dimethyl-4-ethoxyphenyl)-N-[1-(1-ethynyl)cyclohexyl]amine

The expected product is obtained according to the procedure described in Step 1 of Example 1, using as starting material the compound described in Preparation C.

Step 2:

5,7-Dimethyl-6-ethoxy-1,2-dihydroquinoline-2-spirocyclohexane hydrochloride

The expected product is obtained according to the procedure described in Step 2 of Example 1, starting from the compound described in the above Step.

Melting point: 175°–180° C. (Et$_2$O); Elemental microanalysis (empirical formula: C$_{18}$H$_{25}$NO.HCl).

|  | C | H | N | Cl |
|---|---|---|---|---|
| % found | 70.47 | 8.55 | 4.57 | 11.56 |
| % calculated | 70.23 | 8.51 | 4.55 | 11.52 |

EXAMPLE 6

6-Ethoxy-2,2,5,7,8-pentamethyl-1,2,3,4-tetrahydroquinoline hydrochloride

Step 1:

N-(1,1-Dimethyl-2-propynyl)-N-(4-ethoxy-2,3,5-trimethylphenyl)amine

The expected product is obtained according to the procedure described in Step 1 of Example 1, using as starting material the compound described in Preparation A and replacing the 1-ethynyl-1-chlorocyclohexane by 2-chloro-2-methyl-3-butyne (prepared according to the method described in J. Am. Chem. Soc., 83, 725, 1961, starting from 2-methyl-3-butyn-2-ol).

Step 2:

6-Ethoxy-2,2,5,7,8-pentamethyl-1,2-dihydroquinoline

The expected product is obtained according to the procedure described in Step 2 of Example 1, starting from the compound described in the above Step.

Step 3:

6-Ethoxy-2,2,5,7,8-pentamethyl-1,2,3,4-tetrahydroquinoline hydrochloride 0.9 g of palladium-on-carbon (10%) is added to a solution of 5.99 mmol (1.47 g) of the compound described in the above Step in 55 ml of ethanol. The reaction mixture is stirred under 1 atm. of hydrogen at ambient temperature for two hours. The reaction mixture is then filtered and the filtrate is concentrated. The expected product is obtained in hydrochloride form by precipitation from ethereal hydrogen chloride.

Elemental microanalysis (empirical formula: C$_{16}$H$_{25}$NO.HCl).

|         | C     | H    | N    | Cl    |
|---------|-------|------|------|-------|
| % found | 67.64 | 9.16 | 5.01 | 12.40 |
| % calculated | 67.71 | 9.23 | 4.93 | 12.49 |

EXAMPLE 7

5,7-Diisopropyl-2,2-dimethyl-6-ethoxy-1,2,3,4-tetrahydroquinoline hydrochloride

Step 1:

N-(1,1-Dimethyl-2-propynyl)-N-(3,5-diisopropyl-4-ethoxyphenyl)amine

The expected product is obtained according to the procedure described in Step 1 of Example 1, using as starting material the compound described in Preparation B and replacing the 1-ethynyl-1-chlorocyclohexane by 2-chloro-2-methyl-3-butyne (prepared according to the method described in J. Am. Chem. Soc., 83, 725, 1961, starting from 2-methyl-3-butyn-2-ol).

Step 2:

5,7-Diisopropyl-2,2-dimethyl-6-ethoxy-1,2-dihydroquinoline

The expected product is obtained according to the procedure described in Step 2 of Example 1, starting from the compound described in the above Step.

Step 3:

5,7-Diisopropyl-2,2-dimethyl-6-ethoxy-1,2,3,4-tetrahydroquinoline hydrochloride

The expected product is obtained according to the procedure described in Step 3 of Example 6, starting from the compound described in the above Step.

Melting point: 227°–230° C. (Et$_2$O). Elemental microanalysis (empirical formula: C$_{19}$H$_{31}$NO.HCl)

|         | C     | H    | N    | Cl    |
|---------|-------|------|------|-------|
| % found | 70.00 | 9.68 | 4.24 | 10.82 |
| % calculated | 70.02 | 9.90 | 4.30 | 10.88 |

EXAMPLE 8

6-Ethoxy-2,2,5,7-tetramethyl-1,2,3,4-tetrahydroquinoline hydrochloride

Step 1:

N-(1,1-Dimethyl-2-propynyl)-N-(3,5-dimethyl-4-ethoxyphenyl)amine

The expected product is obtained according to the procedure described in Step 1 of Example 1, using as starting material the compound described in Preparation C and replacing the 1-ethynyl-1-chlorocyclohexane by 2-chloro-2-methyl-3-butyne (prepared according to the method described in J. Am. Chem. Soc., 83, 725, 1961, starting from 2-methyl-3-butyn-2-ol).

Step 2:

6-Ethoxy-2,2,5,7-tetramethyl-1,2-dihydroquinoline

The expected product is obtained according to the procedure described in Step 2 of Example 1, starting from the compound described in the above Step.

Step 3:

6-Ethoxy-2,2,5,7-tetramethyl-1,2,3,4-tetrahydroquinoline hydrochloride

The expected product is obtained according to the procedure described in Step 3 of Example 6, starting from the compound described in the above Step.

Melting point: 198°–200° C. (Et$_2$O) Elemental microanalysis (empirical formula: C$_{19}$H$_{31}$NO.HCl)

|         | C     | H    | N    | Cl    |
|---------|-------|------|------|-------|
| % found | 66.71 | 8.93 | 5.15 | 13.11 |
| % calculated | 66.77 | 8.97 | 5.19 | 13.35 |

EXAMPLE 9

6-Ethoxy-5,7,8-trimethyl-1,2,3,4-tetrahydroquinoline-2-spirocyclohexane hydrochloride The expected product is obtained according to the procedure described in Step 3 of Example 6, using as starting material the compound described in Example 2.

Melting point: 192°–198° C. (with decomposition; EtOH); Elemental microanalysis (empirical formula: C$_{19}$H$_{29}$NO.HCl).

|         | C     | H    | N    | Cl    |
|---------|-------|------|------|-------|
| % found | 70.46 | 9.23 | 4.35 | 10.98 |
| % calculated | 70.46 | 9.34 | 4.32 | 10.95 |

EXAMPLE 10

6-Ethoxy-1,2-dihydroquinoline-2-spiro-4'-piperidine hydrochloride

Step 1:

tert-Butyl 4-[(4-ethoxyphenyl)imino]-1-piperidinecarboxylate 45 g of molecular sieve (5 Å) are added to a solution of 202.6 mmol (27.8 g) of paraphenetidine and 169 mmol (33.7 g) of N-tert-butoxycarbonyl-4-piperidone in 60 ml of ether. The whole is stirred at ambient temperature for 15 hours. The reaction mixture is subsequently filtered and then the filtrate is concentrated to yield the expected product.

Step 2:

tert-Butyl 4-(4-ethoxyaniline)-4-(2-trimethylsilyl-1-ethynyl)-1-piperidinecarboxylate 66.7 mmol (42 ml) of a 1.6M solution of n-butyllithium are added dropwise in the course of 1 hour to a solution, cooled to −78° C., of 77.8 mmol (7.64 g) of trimethylsilylacetylene in 160 ml of THF. The whole is stirred at −78° C. for 1 hour and then at ambient temperature for a further hour. The lithium trimethylsilylacetylide so formed is then added dropwise to 155.5 mmol (49.5 g) of the compound described in the above Step dissolved in 500 ml of THF. The reaction mixture is stirred at −78° C. for 1 hour and then at ambient temperature for 15 hours. The reaction mixture is then poured into a mixture of ethyl acetate and ice. The organic phase is isolated, washed with ammonium chloride (10%), dried and then concentrated. The oily residue obtained is purified by chromatography on silica gel, using a petroleum ether: ethyl acetate mixture (4:1) as eluant, to yield the expected compound.

Step 3:

tert-Butyl 4-(4-ethoxyanilino)-4-(1-ethynyl)-1-piperidinecarboxylate 23.7 mmol (24 ml) of a 1M solution of tetrabutylammonium fluoride in THF are added dropwise to a solution, cooled to 0° C., of 21.38 mmol (8.91 g) of the compound described in the above Step in 270 ml of THF. After stirring for 1 hour at 0° C., the mixture is diluted with ether and then washed with water. The organic phase is dried and then concentrated and the residue is purified by chromatography on silica gel, using a petroleum ether:ethyl acetate mixture (4:1) as eluant, to yield the expected product.

Step 4:

6-Ethoxy-1,2-dihydroquinoline-2-spiro-4'-(1'-tert-butoxycarbonyl-piperidine)

The expected product is obtained according to the procedure described in Step 2 of Example 1, starting from the compound described in the above Step.

Step 5:

6-Ethoxy-1,2-dihydroquinoline-2-spiro-4'-piperidine hydrochloride 30 ml of concentrated hydrochloric acid solution are added at ambient temperature to a solution of 5.99 mmol (2.06 g) of the compound described in the above Step in 100 ml of absolute EtOH. After stirring for 1 hour 30 minutes, the solvents are evaporated off and the residue is taken up in an ethyl acetate/water mixture. The two-phase solution is brought to pH=11 using 2M sodium hydroxide solution. The organic phase is isolated and then dried and concentrated to yield the expected product.

The corresponding hydrochloride is obtained by precipitation from an ether/dichloromethane mixture to which ethereal hydrogen chloride is added.

Elemental microanalysis (empirical formula: $C_{15}H_{20}N_2O.HCl$).

|  | C | H | N | Cl |
|---|---|---|---|---|
| % found | 63.47 | 7.58 | 9.66 | 13.58 |
| % calculated | 64.16 | 7.54 | 9.98 | 12.63 |

EXAMPLE 11

6-Ethoxy-1,2-dihydroquinoline-2-spiro-4'-(1'-cyclopropylmethyl-piperidine) hydrochloride 2.45 mmol (0.23 ml) of bromomethylcyclopropane are added, in the presence of 4 mmol (0.56 g) of potassium carbonate, to a solution of 2 mmol (0.5 g) of the compound described in Example 10 in 30 ml of acetonitrile. The mixture is stirred at ambient temperature for 15 hours before being filtered. The filtrate is concentrated and the residue is purified by chromatography on silica gel, using a dichloromethane:ethanol mixture 9:1 as eluant, to yield the expected product. The corresponding hydrochloride is obtained by precipitation from an ethereal hydrogen chloride/dichloromethane mixture.

Melting point: 170° C. (with decomposition; $Et_2O$); Elemental microanalysis (empirical formula: $C_{15}H_{20}N_2O.1.6HCl$).

|  | C | H | N | Cl |
|---|---|---|---|---|
| % found | 64.36 | 7.50 | 7.86 | 16.20 |
| % calculated | 63.96 | 7.81 | 7.85 | 15.90 |

EXAMPLE 12

2,2-Dimethyl-6-ethoxy-3-(2-morpholinoethyl)-1,2-dihydroquinoline dihydrochloride Step 1:

1-Acetyl-2,2-dimethyl-6-ethoxy-1,2-dihydroquinoline

A solution of 30.2 mmol (6.15 g) of 2,2-dimethyl-6-ethoxy-1,2-dihydroquinoline (prepared according to the procedure described in Steps 1 and 2 of Example 1 starting from 2-chloro-2-methyl-3-butyne) in 45 ml of acetic anhydride is heated at 100° C. under an inert atmosphere for 3 hours. After cooling, the medium is concentrated and the residue is purified by chromatography on silica gel, using a dichloromethane:ethyl acetate mixture 95:5 as eluant, to yield the expected compound.

Step 2:

1-Acetyl-3-bromo-2,2-dimethyl-6-ethoxy-4-hydroxy-1,2,3,4-tetrahydroquinoline 28.37 mmol (5.05 g) of N-bromosuccinimide are added in portions to a solution, cooled to 0° C., of 24.7 mmol (6.06 g) of the compound described in the above Step in 154 ml of a dimethyl sulphoxide:water mixture 10:1. The reaction mixture is subsequently diluted with ethyl acetate and then washed 3 times with 100 ml of water and once with 100 ml of saturated sodium chloride solution. The organic phase is dried and concentrated to yield the expected compound.

Step 3:

1-Acetyl-3-bromo-2,2-dimethyl-6-ethoxy-1,2,3,4-tetrahydroquinolin-4-one 30 g of activated molecular sieve 4 Å are added to a solution of 24.51 mmol (8.39 g) of the compound described in the above Step in 225 ml of dichloromethane. The reaction mixture is cooled to 0° C. and 31.10 mmol (23 g) of pyridinium dichromate are added thereto in portions. The reaction mixture is stirred at 0° C. for 10 minutes and then at ambient temperature for 2 hours. The mixture is filtered and the precipitate is rinsed with dichloromethane and with acetone. The filtrate is concentrated and purified by chromatography on silica gel, using a petroleum ether:ethyl acetate mixture 70:30 as eluant, to yield the expected compound.

Step 4:

1-Acetyl-2,2-dimethyl-6-ethoxy-3-[(ethoxycarbonyl-tert-butoxycarbonyl)-methyl]1,2,3,4-tetrahydroquinolin-4-one 32.35 mmol (6.09 g) of tert-butyl ethyl malonate dissolved in 30 ml of THF are added dropwise to a suspension, cooled to 0° C., of 29.75 mmol (1.19 g) of sodium hydride 60% in oil in 85 ml of THF. After stirring for 30 minutes at 0° C., 21.57 mmol (7.34 g) of the compound described in the above Step dissolved in 35 ml of THF are added dropwise. The reaction mixture is stirred for 10 minutes at 0° C. and then at ambient temperature for 3 hours. The reaction mixture is neutralised with 100 ml of water and the medium is diluted with ethyl acetate. The organic phase is washed with saturated sodium chloride solution, dried, concentrated and purified by chromatography on silica gel, using a petroleum ether:ethyl acetate mixture 80:20 as eluant, to yield the expected compound.

Step 5:

1-Acetyl-2,2-dimethyl-6-ethoxy-3-(ethoxycarbonylmethyl)-1,2,3,4-tetrahydroquinolin-4-one 118.1 mmol (9.1 ml) of trifluoroacetic acid are added to a solution, cooled to 0° C., of 5.9 mmol (2.64 g) of the compound described in the above Step in 90 ml of dichloromethane. The reaction mixture is stirred at ambient temperature for 15 hours. The medium is subsequently diluted with ethyl acetate and then washed with saturated $NaHCO_3$ solution. The organic phase is removed, and the aqueous phase is brought to pH=1 using concentrated hydrochloric acid solution and then extracted with ethyl acetate. The organic phase is dried and concentrated. The residue is taken up in 110 ml of dioxane and the mixture is heated at reflux for 9 hours. The solvent is evaporated off and the residue is purified by chromatography on silica gel, using a petroleum ether:ethyl acetate mixture 70:30 as eluant, to yield the expected compound.

Step 6:

2,2-Dimethyl-6-ethoxy-4-hydroxy-3-(2-hydroxyethyl)-1,2,3,4-tetrahydroquinoline 1.50 ml of water and 5.05 mmol (0.96 g) of p-toluenesulphonic acid are added to a solution of 10.05 mmol (0.96 g) of the compound described in the above Step in 60 ml of toluene. The whole is heated at reflux for 2 hours and then the solvents are evaporated off. The residue is taken up in ethyl acetate and washed with saturated $NaHCO_3$ solution. The organic phase is dried and concentrated. The product obtained is dissolved in 15 ml of THF and added to 27.9 mmol (1.06 g) of lithium aluminium hydride suspended in 100 ml of THF. After stirring for one hour at ambient temperature, the reaction mixture is cooled using an ice bath, and 1 ml of water and 1 ml of 15% sodium hydroxide solution are added. The mixture is then filtered and the filtrate is concentrated to yield the expected compound.

Step 7:

2,2-Dimethyl-6-ethoxy-3-(2-hydroxyethyl)-1,2-dihydroquinoline

A solution of 1.73 mmol (0.46 g) of the compound described in the above Step in 1 ml of dimethyl sulphoxide is heated at 170° C. for 1 hour 30 minutes. The mixture is cooled and then diluted with ethyl acetate. After washing with water, the organic phase is dried, concentrated and purified by chromatography on silica gel, using a petroleum ether:ethyl acetate mixture 70:30 as eluant, to yield the expected compound.

Step 8: 3-(2-Bromoethyl)-2,2-dimethyl-6-ethoxy-1,2-dihydroquinoline 5.73 mmol (1.9 g) of carbon tetrabromide are added to a solution of 3.68 mmol (0.91 g) of the compound described in the above Step in 20 ml of dichloromethane. The whole is cooled to 0° C. and 5.71 mmol (1.75 g) of triphenylphosphine dissolved in 15 ml of dichloromethane are added. The reaction mixture is stirred at 0° C. for 15 minutes and at ambient temperature for 2 hours. The solvent is evaporated off and the residue obtained is purified by chromatography on silica gel, using dichloromethane as eluant, to yield the expected compound.

Step 9:

2,2-Dimethyl-6-ethoxy-3-(2-morpholinoethyl)-1,2-dihydroquinoline dihydrochloride 2.15 mmol (0.19 g) of morpholine are added to a solution of 0.69 mmol (0.21 g) of the compound described in the above Step in 1 ml of acetonitrile. The reaction mixture is stirred at ambient temperature for 15 hours. The medium is then diluted with ethyl acetate and washed with water The organic phase is dried, concentrated and purified by chromatography on silica gel, using a dichloromethane:ethanol mixture 95:5 as eluant, to yield the expected compound. The latter is dissolved in ethyl acetate and a 3M solution of hydrochloric acid in ethyl acetate is added slowly. After stirring for 15 minutes, the solvent is evaporated off and the residue is taken up in isopropanol, washed and filtered to yield the expected dihydrochloride.

Elemental microanalysis (empirical formula: $C_{19}H_{28}N_2O_2$.2 HCl).

|  | C | H | N | Cl |
|---|---|---|---|---|
| % found | 58.51 | 7.80 | 7.04 | 18.23 |
| % calculated | 58.61 | 7.77 | 7.19 | 18.21 |

EXAMPLE 13

6-tert-Butoxy-1,2-dihydroquinoline-2-spirocyclohexane hydrochloride

Step 1:

N-(4-tert-Butoxyphenyl)-N-[1-(1-ethynyl)cyclohexyl]amine

The expected product is obtained according to the procedure described in Step 1 of Example 1, starting from the compound described in Preparation D.

Step 2:

6-tert-Butoxy-1,2-dihydroquinoline-2-spirocyclohexane hydrochloride

The expected product is obtained according to the procedure described in Step 2 of Example 1, starting from the compound described in the above Step. The corresponding hydrochloride is obtained by precipitation from ethyl acetate after addition of HCl in ethyl acetate (3M).

Melting point: 132° C. (AcOEt); Elemental microanalysis (empirical formula: $C_{18}H_{25}NO.HCl$).

|  | C | H | N | Cl |
|---|---|---|---|---|
| % found | 70.03 | 8.57 | 4.43 | 11.34 |
| % calculated | 70.23 | 8.51 | 4.55 | 11.52 |

EXAMPLE 14

6-Methoxy-1,2-dihydroquinoline-2-spirocyclohexane hydrochloride

Step 1

N-(2-Methoxyphenyl)-N-[1-(1-ethynyl)cyclohexyl]amine

The expected product is obtained according to the procedure described in Step 1 of Example 1, with replacement of the p-phenetidine by p-anisidine.

Step 2:

6-Methoxy-1,2-dihydroquinoline-2-spirocyclohexane hydrochloride

The expected product is obtained according to the procedure described in Step 2 of Example 1, starting from the compound described in the above Step. The corresponding hydrochloride is obtained by precipitation from ethyl acetate after addition of HCl in ethyl acetate (3M).

Melting point: 191° C. (AcOEt); Elemental microanalysis (empirical formula: $C_{15}H_{19}NO.HCl$).

|   | C | H | N | Cl |
|---|---|---|---|---|
| % found | 67.31 | 7.59 | 5.11 | 13.42 |
| % calculated | 67.79 | 7.58 | 5.27 | 13.34 |

EXAMPLE 15

6-Phenoxy-1,2-dihydroquinoline-2-spirocyclohexane hydrochloride

Step 1:

N-(2-Phenoxyphenyl)-N-[1-(1-ethynyl)cyclohexyl]amine

The expected product is obtained according to the procedure described in Step 1 of Example 1, with replacement of the p-phenetidine by 4-phenoxyaniline.

Step 2:

6-Phenoxy-1,2-dihydroquinoline-2-spirocyclohexane hydrochloride

The expected product is obtained according to the procedure described in Step 2 of Example 1, starting from the compound described in the above Step. The corresponding hydrochloride is obtained by precipitation from ethyl acetate after addition of HCl in ethyl acetate (3M).

Melting point: 176° C. (AcOEt); Elemental microanalysis (empirical formula: $C_{20}H_{21}NO.HCl$).

|   | C | H | N | Cl |
|---|---|---|---|---|
| % found | 73.36 | 6.84 | 4.43 | 10.75 |
| % calculated | 73.27 | 6.76 | 4.27 | 10.81 |

EXAMPLE 16

6-Ethoxy-5,7-dimethyl-1,2,3,4-tetrahydroquinoline-2-spirocyclo-hexane hydrochloride The expected product is obtained according to the procedure described in Example 6, Step 3, using as starting material the compound described in Example 5.

Elemental microanalysis (empirical formula: $C_{18}H_{27}NO.HCl$).

|   | C | H | N | Cl |
|---|---|---|---|---|
| % found | 69.27 | 9.11 | 4.52 | 11.44 |
| % calculated | 69.57 | 9.21 | 4.48 | 11.72 |

EXAMPLE 17

6-Ethoxy-2,2-dimethyl-3-[2-(2,6-dioxopiperazin-4-yl)ethyl]-1,2-dihydroquinoline hydrochloride The expected product is obtained according to the procedure described in Example 12, with replacement of the morpholine by 2,6-dioxopiperazine in Step 9.

Elemental microanalysis.

|   | C | H | N | Cl |
|---|---|---|---|---|
| % found | 54.81 | 6.54 | 10.09 | 17.03 |
| % calculated | 55.26 | 6.49 | 10.07 | 16.46 |

EXAMPLE 18

6-Ethoxy-2,2-dimethyl-3-[2-(1-piperidinyl)ethyl]-1,2-dihydroquinoline hydrochloride The expected product is obtained according to the procedure described in Example 12, with replacement of the morpholine by piperazine in Step 9.

EXAMPLE 19

2-[2-(6-Ethoxy-2,2-dimethyl-1,2-dihydro-3-yl) ethyl]-1H-isoindole-1,3(2H)-dione hydrochloride The expected product is obtained according to the procedure described in Example 12, with replacement of the morpholine by phthalimide in Step 9.

EXAMPLE 20

3-[2-(6-Ethoxy-2,2-dimethyl-1,2-dihydro-3-quinolenyl)ethyl]-4(3H)-quinazolinone hydrochloride The expected product is obtained according to the procedure described in Example 12, with replacement of the morpholine by 4(3H)-quinazolinone in Step 9.

EXAMPLE 21

6-tert-Butylcarbonyloxy-1,2-dihydroquinoline-2-spirocyclohexane hydrochloride Step 1:

N-(2-tert-Butylcarbonyloxy)-N-[1-(1-ethynyl)cyclohexyl]amine

The expected product is obtained according to the procedure described in Step 1 of Example 1, starting from the compound described in Preparation E.

Step 2:

6-tert-Butylcarbonyloxy-1,2-dihydroquinoline-2-spirocyclohexane hydrochloride

The expected product is obtained according to the procedure described in Step 2 of Example 1, starting from the compound described in the above Step. The corresponding hydrochloride is obtained by precipitation from ethyl acetate after addition of HCl in ether (1.3M).

Melting point: 180° C. ($Et_2O$/AcOEt); Elemental microanalysis (empirical formula: $C_{19}H_{25}NO_2.HCl$).

|   | C | H | N | Cl |
|---|---|---|---|---|
| % found | 68.13 | 7.90 | 4.07 | 10.38 |
| % calculated | 67.94 | 7.80 | 4.17 | 10.56 |

PHARMACOLOGICAL STUDY

EXAMPLE A

Cytotoxicity Test Using L-homocysteine on Murine HT22 Hippocampal Cells

Murine HT22 hippocampal cells in culture (100 µl/well DMEM/F-12/25% FCS) are preincubated for 1 hour in the presence of 2 concentrations (0.1 and 0.5 μM) of the compound being studied. The cell cultures are then exposed for 48 hours to 2 mM L-homocysteine in the presence or in the absence of the compound being tested. The cytotoxicity is evaluated by the 3-(4,5-dimethylthiazol-2-yl)-2,5-diphenyl-tetrazolium bromide (MTT) reduction method (Mosmann T., Immunol. Methods. 65:55–63 (1983)). The results are expressed as % of protection compared with the cytotoxicity measured in the cell cultures in the absence of the compound being tested. It appears that, at 0.5 μM, most of the compounds of the invention have a percentage of protection of 100%.

EXAMPLE B

Lethality Test Using tert-butylhydroperoxide in the NMRI Mouse

Intracerebroventricular (icv) administration of tert-butylhydroperoxide (1 μl of a 70% solution) causes lethality in the adult male NMRI mouse (30–35 g). The lethality is measured 2 hours after the administration of tert-butylhydroperoxide and is expressed as a percentage of protection compared with the lethality in the animals that have been given the carrier of the compounds studied. The latter are administered by the intraperitoneal route in a dose of 150 mg/kg i.p. 30 minutes before the administration of tert-butylhydroperoxide.

It appears that, for most of the compounds of the invention, the percentage of protection measured is from 70 to 100%.

EXAMPLE C

Evaluation of the Effects on Body Temperature in the NMRI Mouse

The body temperature in adult male NMRI mice (25–30 g) is measured using a rectal probe (Physitemp, Bat-12) 30, 60, 90 and 120 minutes after the administration by the intraperitoneal route of the compounds studied in a dose of 150 mg/kg. The results are expressed as the average maximum difference in temperature (° C.) determined in the treated animals compared with the control animals, which have received only the carrier (20 ml/kg).

The results show that, at a neuroprotective dose, compounds of the invention do not induce a hypothermic effect or induce only a slight hypothermic effect.

EXAMPLE D

Antagonism of Dopaminergic Striatonigral Dysfunctions Induced by Administration of Methamphetamine in the $C_{57}BL/6$ Mouse Male mice (C57BL/6 20–25 g) are given four injections of d-methamphetamine (5 mg/kg base, i.p.) at intervals of 2 hours (Sonsalla and Heikkila, Prog. Neuro-Psychopharmacolo. & Biol. Psychiat., 12, 345–354, 1988) and the anti-oxidant being tested is administered (i.p.) 30 minutes before the first and third injections of d-methamphetamine (Yamamoto and Zhu, J. Pharmacol. Exp. Ther. 287, 107–114, 1988). The rectal temperature is monitored throughout the duration of the experiment. The animals are sacrificed by decapitation 72 hours after the last injection of d-methamphetamine. The brains are rapidly extracted, and the striata are removed, frozen in liquid nitrogen and weighed. The striata are homogenised by sonication in 20 volumes of 0.1N $HClO_4$, and the homogenate is centrifuged at 15000 g for 20 minutes at 4° C. The supernatants are collected for assaying the striata tissue levels of dopamine by means of HPLC coupled with coulometric detection (Bonhomme et al., Brain Res., 675, 215–233, 1995). The results are expressed as μg of dopamine/g of tissue. It appears that the compounds of the invention oppose the dopaminergic deficit induced by the administration of methamphetamine. That is true especially of the compound of Example 1 administered in a dose of 2×150 mg/kg i.p.

EXAMPLE E

Neuroprotection in the Case of Transient and Global Cerebral Ischaemia in the Wistar Rat This animal model (Pulsinelli and Brierley, Stroke 10, 267–272, 1979), is commonly used for the detection of central anti-ischaemic agents (Buchan et al., Neurosci. Lett., 132(2), 255–258, 1991).

Under pentobarbital anaesthesia, the vertebral arteries of male Wistar rats (280–320 g, Charles River) are permanently occluded by electrocoagulation and carotid ligatures are placed around each common carotid. 24 hours later, ischaemia is brought about for minutes by clamping the carotids with the carotid ligatures. This ischaemic episode causes delayed neurone death at the level of the pyramidal cells of the hippocampus. Neurone death is measured by a neurone count on sections of brain (7 μm, staining: hematoxylin-eosin) of rats sacrificed 7 days after the ischaemic episode. The results are expressed as a percentage of viable hippocampal neurones compared with the total hippocampal neurone population. It appears that the compounds of the invention significantly reduce hippocampal neurone death which follows ischaemia. That is true especially of the compound of Example 1, which, on administration 30 minutes before the start of the ischaemia, induces a reduction by a factor of 2.7.

EXAMPLE F

Delayed Hippocampal Neurodegeneracy Induced by Administration of Kainic Acid in the Wistar Rat This method is frequently used as a model of temporal epilepsy in humans (Ben-Ari, Neurosci., 14, 375–403, 1985).

Male Wistar rats (180–220 g, CERJ) are given kainic acid (12 mg/kg) by the subcutaneous route. The animals are sacrificed by decapitation 7 days later. The brains are removed and then cut, in the frozen state, into frontal sections of 7 μm, which are stained (hematoxylin-eosin). Hippocampal neurone death is assessed by a neurone count at the level of the $CA_3$ layer of the hippocampus. The results are expressed as a percentage of viable neurones in the $CA_3$ layer compared with the total neurone population.

It appears that the compounds of the invention significantly reduce neurone death in the $CA_3$ layer of the hippocampus. In particular, the compound of Example 1, administered in a dose of 150 mg/kg i.p. 30 minutes before the administration of kainic acid, induces a reduction in neurone death by a factor of 3.

EXAMPLE G

Pharmaceutical Composition

Formulation for the preparation of 1000 tablets each comprising 10 mg of active ingredient

| | |
|---|---|
| Compound of Example 1 | 10 g |
| Hydroxypropyl cellulose | 2 g |
| Wheat starch | 10 g |
| Lactose | 100 g |
| Magnesium stearate | 3 g |
| Talc | 3 g |

We claim:

1. A compound selected from those of formula (I):

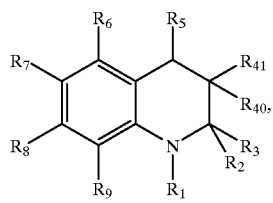

wherein:

$R_1$ represents hydrogen or

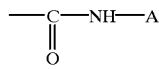

wherein A represents hydrogen or —$BNZ_1Z_2$ in which B represents linear or branched ($C_1$–$C_6$)alkylene and $Z_1$ and $Z_2$ independently represent hydrogen or alkyl, ($C_3$–$C_8$)cycloalkyl, or optionally substituted aryl or, together with the nitrogen atom carrying them, form an optionally substituted heterocycloalkyl or heteroaryl, $R_2$ and $R_3$ each independently represents alkyl, ($C_3$–$C_8$)cycloalkyl, heterocycloalkyl, optionally substituted aryl, optionally substituted heteroaryl, cycloalkylalkyl, heterocycloalkylalkyl, optionally substituted arylalkyl, optionally substituted heteroarylalkyl, or aminoalkyl optionally substituted on the nitrogen by one or two groups selected from alkyl, cycloalkyl, aryl, and arylalkyl or $R_2$ and $R_3$ together with the carbon atom carrying them, form a ($C_3$–$C_8$)cycloalkyl or a monocyclic heterocycloalkyl unsubstituted or substituted by alkyl, cycloalkyl, cycloalkylalkyl, aryl, or arylalkyl, $R_{40}$ represents hydrogen or a group selected from optionally substituted alkyl, optionally substituted alkenyl, and optionally substituted alkynyl, or a group Q or —V—Q wherein V represents alkylene, alkenylene, or alkynylene, and Q represents optionally substituted cycloalkyl, optionally substituted aryl, optionally substituted heterocycloalkyl, or optionally substituted heteroaryl, $R_{41}$ and $R_5$ together form a bond or each represents hydrogen, $R_6$, $R_7$, $R_8$ and $R_9$ each independently represents hydrogen, halogen, alkyl, ($C_3$–$C_8$)cycloalkyl, or —OW wherein W represents hydrogen, alkyl, ($C_3$–$C_8$)cycloalkyl, heterocycloalkyl, optionally substituted aryl, optionally substituted heteroaryl, optionally substituted arylalkyl, or optionally substituted heteroarylalkyl provided that $R_6$, $R_7$, $R_8$ and $R_9$ cannot all simultaneously represent hydrogen and that at least one of them represents —OW as defined hereinbefore, with the proviso that:

$R_2$ and $R_3$ represent alkyl:
if each of $R_6$ to $R_9$ independently represents hydrogen, alkyl or —OW wherein W represents alkyl, and $R_{41}$ and $R_5$ together form a bond, then $R_{40}$ is other than hydrogen or alkyl, if a single group —OW is present in the molecule and represents hydroxy, then $R_{40}$ is other than hydrogen, if a single group —OW is present in the molecule and represents methoxy, then $R_{40}$ is other than hydroxyalkyl, the compound of formula (I) being other than 7-methoxy-2,2-diphenyl-1,2-dihydroquinoline, when $R_2$ and $R_3$ are methyl, $R_1$, $R_{41}$ and $R_5$ are hydrogen, then $R_7$ is hydrogen, halogen, alkyl, ($C_3$–$C_8$)cycloalkyl, or —OW wherein W represents hydrogen, ($C_2$–$C_8$)alkyl, ($C_3$–$C_8$)cycloalkyl, heterocycloalkyl, optionally substituted aryl, optionally substituted heteroaryl, optionally substituted arylalkyl, or optionally substituted heteroarylalkyl, when $R_2$ and $R_3$, together with the carbon atom carrying them, form a cyclohexyl and $R_6$, $R_7$, and $R_8$ represent hydrogen, then $R_8$ is hydrogen, halogen, alkyl, ($C_3$–$C_8$)cycloalkyl, or —OW wherein W represents hydrogen, ($C_2$–$C_8$)alkyl, ($C_3$–$C_8$)cycloalkyl, heterocycloalkyl, optionally substituted aryl, optionally substituted heteroaryl, optionally substituted arylalkyl, or optionally substituted heteroarylalkyl, when $R_2$ and $R_3$ represent alkyl and one or two of $R_6$, $R_7$, $R_8$, and $R_9$ is methoxy, then $R_{40}$ represents hydrogen or a group selected from optionally substituted alkyl, optionally substituted alkenyl, and optionally substituted alkynyl, or a group Q or —V—Q wherein V represents alkylene, alkenylene, or alkynylene, and Q represents optionally substituted cycloalkyl, optionally substituted aryl, optionally substituted heterocycloalkyl, or optionally substituted heteroaryl, wherein alkyl may not be hydroxyalkyl, the compound of formula (I) being other than 6-methoxy-2,2-diphenyl-1,2-dihydroquinoline or 7-methoxy-2,2-diphenyl-1,2-dihydroquinoline, and an enantiomer or diastereoisomer thereof, and an addition salt thereof with a pharmaceutically-acceptable acid or base.

2. A compound of claim 1, wherein $R_1$ represents hydrogen.

3. A compound of claim 1, wherein $R_6$, $R_7$, $R_8$ and $R_9$ each independently represents hydrogen, alkyl, or —OW wherein W represents alkyl, acyl, or phenyl.

4. A compound of claim 1, wherein $R_2$ and $R_3$ each represents alkyl.

5. A compound of claim 1, wherein $R_2$ and $R_3$ together form an optionally substituted cycloalkyl or heterocycloalkyl.

6. A compound of claim 1, wherein $R_{40}$ represents hydrogen or V—Q, V being alkylene and Q being heterocycloalkyl.

7. A compound of claim 1, wherein $R_1$ represents hydrogen, $R_2$ and $R_3$ represent alkyl or together form a cycloalkyl, $R_{40}$ represents hydrogen or —V—Q wherein V represents alkylene and Q represents heterocycloalkyl, and $R_6$, $R_7$, $R_8$ and $R_9$ each independently represents hydrogen, alkyl or —OW wherein W represents alkyl, acyl, or phenyl, it being understood that $R_6$, $R_7$, $R_8$ and $R_9$ cannot all represent hydrogen and that at least one of them represents —OW as defined hereinbefore.

8. A compound of claim 7, wherein $R_2$ and $R_3$ together form cycloalkyl.

9. A compound of claim 7, wherein $R_2$ and $R_3$ represent alkyl.

10. A compound of claim 1 which is selected from 6-ethoxy-2,2,5,7,8-pentamethyl-1,2,3,4-tetrahydroquinoline, and an addition salt thereof with a pharmaceutically acceptable acid.

11. A compound of claim 1 which is selected from 6-ethoxy-1,2-dihydroquinoline-2-spirocyclohexane, and an addition salt thereof with a pharmaceutically acceptable acid.

12. A pharmaceutical composition useful as antioxidation agent in the treatment of disorders associated with aging, in the treatment of cognitive disorders, in the treatment of acute neurodegenerative disorders, and in the treatment of chronic neurodegenerative disorders, comprising as active principle an effective amount of a compound as claimed in claim 1, together with one or more pharmaceutically-acceptable excipients or vehicles.

13. A method for treating a living body afflicted with a condition requiring an antioxidation agent and selected from the group consisting of atherosclerosis, cataract, cognitive disorders, acute neurodegenerative disorders, chronic neurodegenerative disorders, and neurodegeneracies of the basal ganglia comprising the step of administering to the living body an amount of a compound of claim 1 which is effective for alleviation of said condition.

14. A method of claim 13, wherein the condition treated is selected from the group consisting of cerebral ischaemia, epilepsy, Alzheimer's disease, Pick's disease, Parkinson's disease, and Huntington's disease.

* * * * *